United States Patent
Yoshioka et al.

(10) Patent No.: US 10,473,609 B2
(45) Date of Patent: Nov. 12, 2019

(54) VITAL INFORMATION MEASUREMENT DEVICE

(71) Applicant: Panasonic Healthcare Holdings Co., Ltd., Tokyo (JP)

(72) Inventors: Eriko Yoshioka, Ehime (JP); Hiroyuki Tokunaga, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 473 days.

(21) Appl. No.: 15/280,159

(22) Filed: Sep. 29, 2016

(65) Prior Publication Data

US 2017/0016846 A1 Jan. 19, 2017

Related U.S. Application Data

(63) Continuation of application No. 13/824,078, filed as application No. PCT/JP2011/006021 on Oct. 27, 2011, now Pat. No. 9,482,636.

(30) Foreign Application Priority Data

Oct. 28, 2010 (JP) ................................ 2010-241638

(51) Int. Cl.
*G01N 27/34* (2006.01)
*G01N 27/327* (2006.01)
(Continued)

(52) U.S. Cl.
CPC ..... *G01N 27/3274* (2013.01); *A61B 5/14532* (2013.01); *C12Q 1/006* (2013.01);
(Continued)

(58) Field of Classification Search
None
See application file for complete search history.

(56) References Cited

U.S. PATENT DOCUMENTS

| 5,352,351 A | 10/1994 | White |
| 2003/0159945 A1 | 8/2003 | Miyazaki |

(Continued)

FOREIGN PATENT DOCUMENTS

| CN | 1486423 A | 3/2004 |
| CN | 1589400 A | 3/2005 |

(Continued)

OTHER PUBLICATIONS

English Translation of International Search Report issued in application No. PCT/JP2011/006021 dated Dec. 6, 2011.
(Continued)

*Primary Examiner* — Eli S Mekhlin
(74) *Attorney, Agent, or Firm* — Pearne & Gordon LLP

(57) ABSTRACT

An objective of the present invention is to provide a vital information measurement device which measures vital information using a biosensor, with which it is possible to adjudicate more precisely whether a mounted biosensor is usable, and to alleviate inconsistency in measured values therefrom. Specifically, the present invention provides a vital information measurement device comprising: an input terminal to which a biosensor is connected; a voltage application unit which applies a voltage to the input terminal; an adjudication unit which is connected to the input terminal; a control unit which is connected to the adjudication unit; and a display unit which is connected to the control unit. The control unit causes the adjudication unit to carry out a first adjudication, a second adjudication, and a third adjudication.

4 Claims, 9 Drawing Sheets

(51) Int. Cl.
    *G01N 27/416*      (2006.01)
    *A61B 5/145*      (2006.01)
    *C12Q 1/00*      (2006.01)
    *G01N 27/26*      (2006.01)
    *G01N 27/28*      (2006.01)
    *A61B 5/1468*      (2006.01)
    *A61B 5/1495*      (2006.01)
    *A61B 5/00*      (2006.01)

(52) U.S. Cl.
    CPC ....... *G01N 27/3272* (2013.01); *G01N 27/416* (2013.01); *A61B 5/1468* (2013.01); *A61B 5/1495* (2013.01); *A61B 5/7246* (2013.01); *A61B 5/742* (2013.01); *G01N 27/26* (2013.01); *G01N 27/28* (2013.01)

(56) References Cited

U.S. PATENT DOCUMENTS

| | | | | |
|---|---|---|---|---|
| 2004/0232009 | A1* | 11/2004 | Okuda | G01N 27/3274 205/789 |
| 2005/0067301 | A1* | 3/2005 | Morita | G01N 27/3274 205/775 |
| 2005/0258034 | A1 | 11/2005 | Iketaki | |
| 2006/0175206 | A1 | 8/2006 | Miyazaki | |
| 2006/0175207 | A1 | 8/2006 | Miyazaki | |
| 2007/0131549 | A1 | 6/2007 | Cai | |
| 2008/0110754 | A1 | 5/2008 | Miyazaki | |
| 2010/0252454 | A1 | 10/2010 | Miyazaki | |
| 2010/0320097 | A1 | 12/2010 | Miyazaki | |
| 2011/0132776 | A1 | 6/2011 | Miyazaki | |
| 2011/0132777 | A1 | 6/2011 | Miyazaki | |

FOREIGN PATENT DOCUMENTS

| | | |
|---|---|---|
| CN | 1991368 a | 7/2007 |
| EP | 0702788 A1 | 3/1996 |
| EP | 1369684 A1 | 12/2003 |
| EP | 1455182 A1 | 9/2004 |
| EP | 2053389 A1 | 4/2009 |
| JP | H08-502589 A | 3/1996 |
| JP | 2003-156469 A | 5/2003 |
| WO | 02/057768 A1 | 7/2002 |
| WO | 03/044513 A1 | 5/2003 |

OTHER PUBLICATIONS

Extended European Search Report issued in application No. EP 11835850 dated Jul. 25, 2014.

* cited by examiner

VITAL INFORMATION MEASUREMENT DEVICE

This is a continuation of U.S. patent application Ser. No. 13/824,078 filed on Mar. 13, 2013 and issued as U.S. Pat. No. 9,482,636 on Nov. 1, 2016, which is the national stage of International Application No. PCT/JP2011/006021 filed on Oct. 27, 2011 which claims priority from Japanese Patent Application No. 2010-241638 filed on Oct. 28, 2010. The contents of these applications are incorporated herein by reference in their entireties.

TECHNICAL FIELD

The claimed invention relates to a vital information measurement device. Vital information represents the concentration or the like of a biological sample, which is a blood-sugar level in blood, for example.

BACKGROUND ART

A configuration of a vital information measurement device in the related art includes an input terminal to which a biosensor is connected, a voltage application section that applies voltage to the input terminal, a determination section that is connected to the input terminal, a control section that is connected to the determination section, and a display section that is connected to the control section (see Patent Literature (hereinafter, abbreviated as PTL) 1, for example).

In the vital information measurement device in the related art, before a blood-sugar level in blood is measured, 1) the biosensor is connected to the input terminal of the vital information measurement device, 2) voltage is applied to the biosensor before being supplied with blood from the voltage application section through the input terminal, and 3) it is determined whether the biosensor is a suitable one. Then, the measurement of the blood-sugar level is performed.

CITATION LIST

Patent Literature

PTL 1: International Patent Application Laid-Open No. 03/044513

SUMMARY OF INVENTION

Technical Problem

The vital information measurement device in the related art as described above informs, in a case where excessive electric current flows in the biosensor when the voltage application is performed, a user that the biosensor is determined to be unusable. The unusable biosensor is a biosensor that is left in a place having high moisture for a long time, for example. Thus, according to the vital information measurement device in the related art, the measurement of the blood-sugar level is not performed using such a biosensor left in the place having high moisture for a long time, but instead, a suitable measurement of the blood-sugar level is performed.

However, according to the vital information measurement device in the related art, even though the blood-sugar level is measured using the biosensor that is determined to be usable, variations may occur in a measurement value. It has been found that one of the reasons why the variation of the measurement value occurs is due to conductive substances adhered to the biosensor. Here, an object of the invention is to provide a vital information measurement device that measures vital information using a biosensor and is capable of appropriately determining whether the mounted biosensor is usable to thereby suppress variation of a measurement value.

Solution to Problem

That is, according to a first aspect of the invention, there is provided a vital information measurement device including an input terminal to which a biosensor is connected, a voltage application section that applies voltage to the input terminal, a measurement section that measures a measurement value based on a value of electric current flowing in the biosensor, a determination section that is connected to the input terminal, a control section that is connected to the determination section, and a display section that is connected to the control section. Here, the measurement section measures a first measurement value and a second measurement value, and measures a third measurement value as necessary. The control section causes the determination section to perform a first determination, a second determination and a third determination.

Firstly, the voltage application section applies voltage to the biosensor connected to the input terminal through the input terminal, and the measurement section measures the first measurement value and the second measurement value based on the value of the electric current flowing in the biosensor. In the first determination, the measured first measurement value or second measurement value is compared with a first threshold value.

The second determination has two types. As the first type, a case where the first measurement value and the second measurement value are obtained while the same voltage is being applied will be described. In this case, in the second determination, the first measurement value or the second measurement value is compared with a second threshold value.

Next, as the second type of the second determination, a case where the first measurement value and the second measurement value are respectively obtained while different voltages are being applied will be described. A measurement value based on the value of the electric current flowing in the biosensor while a first voltage is being applied is used as the first measurement value, and a measurement value based on the value of the electric current flowing in the biosensor while a second voltage is being applied is used as the second measurement value. In this case, in the second determination, the measured first measurement value or second measurement value is compared with the second threshold value.

Normally, since the first measurement value is equal to or higher than the second measurement value (see FIG. 6), the first measurement value and the second threshold value may be compared with each other. However, in a case where the first measurement value is smaller than the second threshold value, the second measurement value and the second threshold value are compared with each other.

The third determination has three types. The third determination may not be performed in a case where both of the first measurement value and the second measurement value is smaller than the second threshold value.

In the first type of the third determination, a difference X between the first measurement value and the second measurement value is compared with a third threshold value. In the second type of the third determination, the voltage application section further applies voltage to the biosensor connected to the input terminal through the input terminal, and the measurement section measures the third measurement value based on the value of the electric current flowing in the biosensor. A difference Y between the first measurement value and the third measurement value is compared with the third threshold value. In the third type of the third determination, a difference Z between the second measurement value and the third measurement value is compared with the third threshold value.

Further, the first threshold value is larger than the second threshold value, and the second threshold value is larger than the third threshold value.

The "measurement value based on the value of the electric current" flowing in the biosensor may be the electric current value itself, may by a voltage value obtained by converting the electric current value by a current-voltage converter, or may be a digital value obtained by converting the voltage value by an A/D converter.

The measurement section may measure the plurality of second measurement values and the plurality of third measurement values for respective different times. In a case where the plurality of second measurement values or the plurality of third measurement values is measured, one measurement value selected from these measurement values may be used for each determination.

For example, the maximum difference among the plurality of differences X between the first measurement value and the plurality of second measurement values may be compared with the third threshold value. Further, the maximum difference among the plurality of differences Y between the first measurement value and the plurality of third measurement values may be compared with the third threshold value; or the maximum difference among the plurality of differences Z between the second measurement value and the plurality of third measurement values may be compared with the third threshold value.

Voltage application may be continuously performed from measurement of the first measurement value to the second measurement value (see Embodiments 1 and 2, in which voltage A (FIG. 4) is formed by one pulse); or an interval where voltage is not applied may be present between voltage application for measurement of the first measurement value and voltage application for measurement of the second measurement value. Similarly, voltage application may be continuously performed from measurement of the second measurement value to the third measurement value (see Embodiment 3, in which voltage A (FIG. 4) is formed by one pulse); or an interval where voltage is not applied may be present between voltage application for measurement of the second measurement value and voltage application for measurement of the third measurement value.

According to a second aspect of the invention, there is provided a method of measuring vital information using the vital information measurement device as described above. A first method thereof includes: a process of connecting the biosensor to the input terminal; a process of applying voltage to the biosensor through the input terminal, by the voltage application section; a process of measuring the first measurement value and the second measurement value based on the value of the electric current flowing in the biosensor; and a process of causing the determination section to perform the first determination, the second determination and the third determination, by the control section (Embodiments 1 and 2). Further, the first threshold value is larger than the second threshold value, and the second threshold value is larger than the third threshold value.

A second method thereof includes: a process of connecting the biosensor to the input terminal; a process of applying voltage to the biosensor through the input terminal, by the voltage application section; a process of measuring the first measurement value, the second measurement value and the third measurement value based on the value of the electric current flowing in the biosensor; and a process of causing the determination section to perform the first determination, the second determination and the third determination, by the control section (Embodiment 3). Further, the first threshold value is larger than the second threshold value, and the second threshold value is larger than the third threshold value.

Advantageous Effects of Invention

According to the vital information measurement device of the invention, it is possible to determine a biosensor that is determined to be usable and causes variation of a measurement value in the vital information measurement device in the related art to be unusable. Thus, according to the vital information measurement device of the invention, it is possible to perform measurement using only a suitable biosensor, and as a result, to suppress variation of a measurement value.

DESCRIPTION OF EMBODIMENTS

[Biological Sample Measurement Device]

A biological sample measurement device according to the invention performs a first determination, a second determination, and a third determination before vital information is measured (before a biological sample is supplied). Thus, the biological sample measurement device determines that a biosensor that is not suitable for measurement of vital information cannot be used, to thereby provide user with a further suitable measurement result.

According to the first determination, it is possible to determine that an excessively deteriorated biosensor is unusable. For example, it is determined that a biosensor that is disposed at a place where the humidity is high for a long time is unusable, according to the first determination. In the first determination, a measurement value based on electric current flowing in the biosensor is compared with a first threshold value, in which the first threshold value is equal to or larger than a second threshold value.

According to the second determination, it is determined whether a deterioration state of the biosensor is such a degree as to be supplied for measurement of vital information, the biosensor being determined to be usable in the first determination. The biosensor that is determined to be unusable for measurement of vital information is supplied for the third determination. When the biosensor determined to be usable for measurement of vital information in the first determination can be determined to be usable according to the second determination, a vital information measurement flow can be started. In the second determination, a measurement value based on electric current flowing in the biosensor is compared with the second threshold value, in which the second threshold value is larger than a third threshold value and is smaller than the first threshold value.

The biosensor determined to be unusable for measurement of vital information in the second determination passes through a determination (third determination) about whether the measurement value based on the electric current flowing in the biosensor decreases with time or does not change. The biosensor determined that the measurement value based on the electric current flowing in the biosensor is not changed is determined to be unusable according to the third determination. In the third determination, the difference between the plurality of measurement values based on the electric current flowing in the biosensor is compared with the third threshold value, in which the third threshold value is smaller than the second threshold value.

Figure 1:
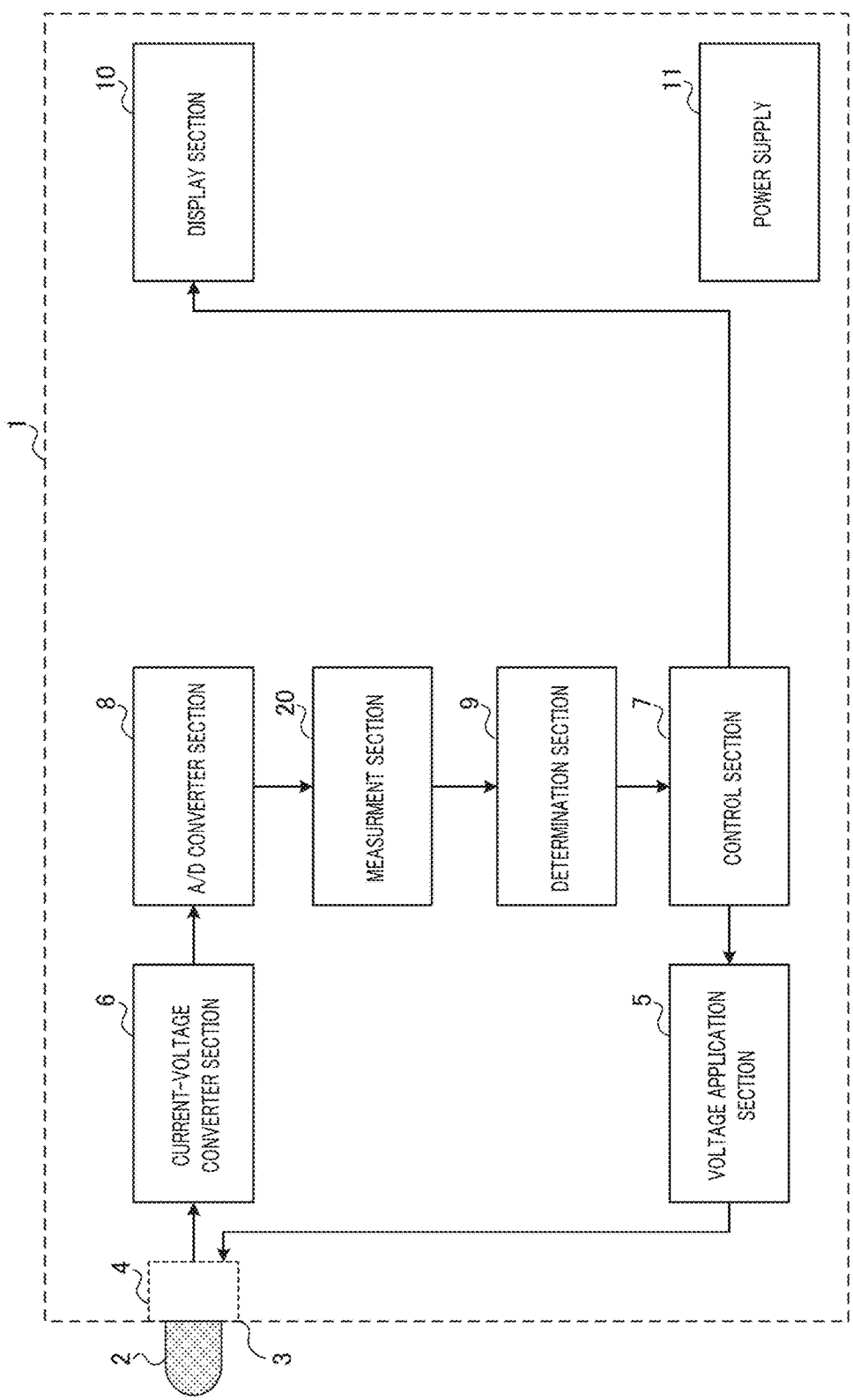
FIG. 1 is a block diagram illustrating a biological sample measurement device according to an embodiment of the invention.

An embodiment of a vital information measurement device according to the invention will be described with reference to FIG. 1. FIG. 1 is a block diagram illustrating a vital information measurement device. Insert port 3 for insertion of biosensor 2 is provided at an end of a main case 1 of the vital information measurement device. Input terminal 4 is provided in insert port 3, and input terminal 4 is configured to be connected to a terminal of biosensor 2 to be mounted. It is preferable that input terminal 4 include two or more terminals, and the terminals are configured to be connected to a counter electrode and an action electrode (see FIG. 2C) of biosensor 2.

Voltage application section 5 capable of applying voltage to input terminal 4 and current-voltage converter section 6 are connected to input terminal 4. Voltage application section 5 applies voltage to input terminal 4 under the control of control section 7 (see voltage A in FIG. 4). If voltage is applied to input terminal 4, electric current flows in biosensor 2. The electric current flowing in biosensor 2 is converted into voltage by current-voltage converter section 6, and the converted voltage is digital-converted by A-D converter section 8. Measurement section 20 measures the digital-converted voltage. Determination section 9 is configured to compare the digital-converted voltage with respective threshold values to be described later (first threshold value, second threshold value and third threshold value).

Figure 4:
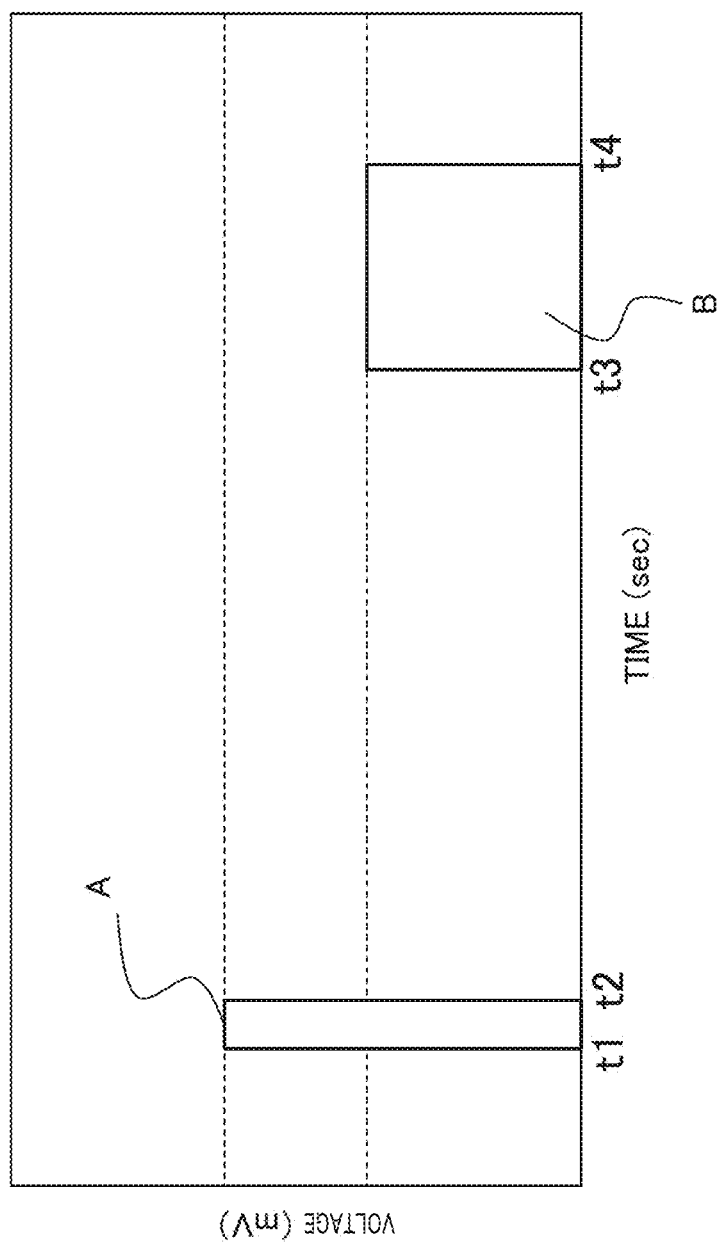
FIG. 4 is a graph illustrating voltage applied to a biosensor by a biological sample measurement device according to an embodiment of the invention.

As shown in FIG. 4, voltage A is formed by only 1 pulse, and a first measurement value and a second measurement value are measured while voltage A is being applied. In this regard, voltage A may be formed by a plurality of pulses. For example, when a first pulse is applied, a first measurement value may be measured, when a second pulse is applied, a second measurement value may be measured, and a third pulse is applied, a third measurement value may be measured. In other words, an interval where voltage is not applied may be present between voltage application for obtaining the first measurement value and voltage application for obtaining the second measurement value, and an interval where voltage is not applied may be present between voltage application for obtaining the second measurement value and voltage application for obtaining the third measurement value.

Further, a plurality of second measurement values may be measured, that is, a plurality of the second measurement values may be measured for respective different times.

Further, a blood-sugar level detected by biosensor 2 or the determination result in determination section 9 are displayed on display section 10 connected to control section 7. Power supply 11 supplies electric power to the respective sections.

[Biosensor]

Figure 2A:
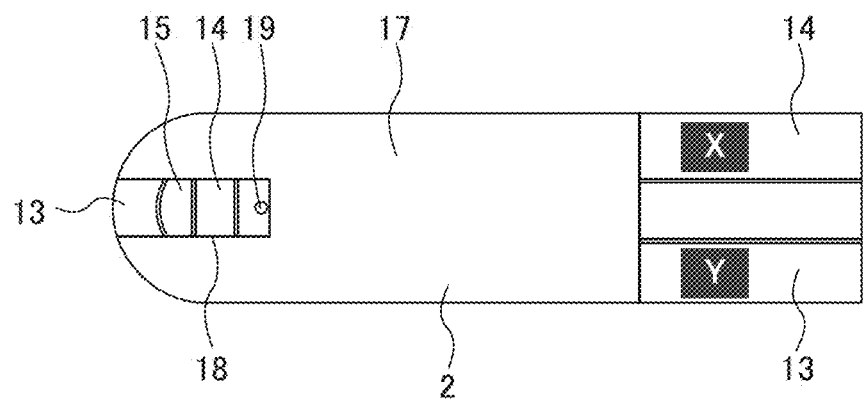
FIG. 2A is a top view illustrating a biosensor used in a biological sample measurement device according to an embodiment of the invention.
Figure 2B:
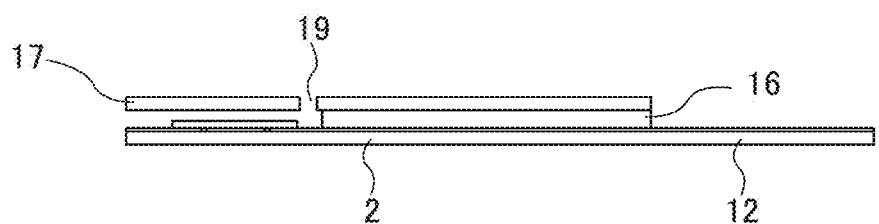
FIG. 2B is a side sectional view illustrating a biosensor used in a biological sample measurement device according to an embodiment of the invention.
Figure 2C:
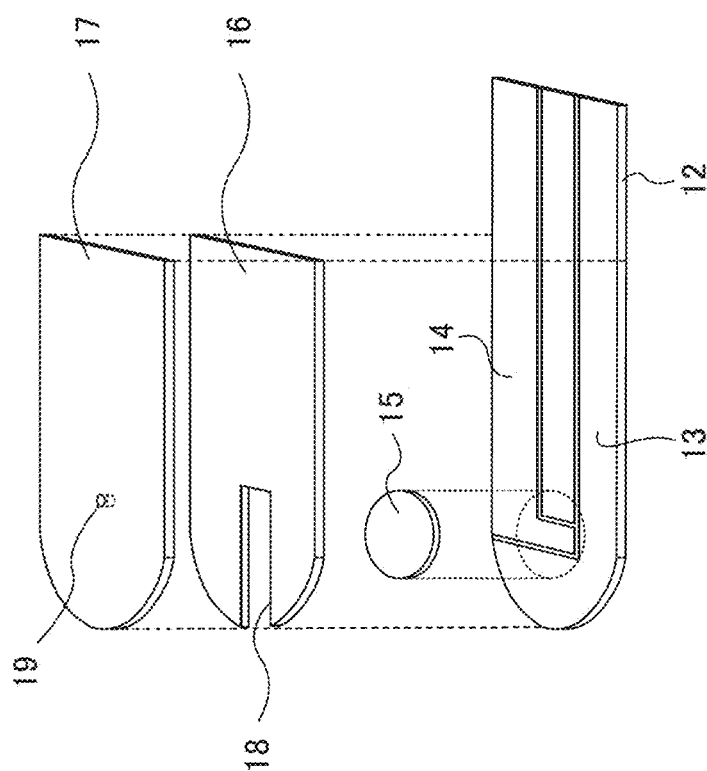
FIG. 2C is an exploded perspective view illustrating a biosensor used in a biological sample measurement device according to an embodiment of the invention.

FIGS. 2A to 2C are a top view (FIG. 2A), a side sectional view (FIG. 2B) and an exploded perspective view (FIG. 2C) of biosensor 2 used in the vital information measurement device according to the invention. As shown in FIGS. 2A to 2C, biosensor 2 may be a plate-shaped member that is integrated by stacking substrate 12, spacer 16 and cover 17.

As shown in FIGS. 2A to 2C, counter electrode 13 and action electrode 14 included in an electrode section are provided on substrate 12. Further, substrate 12 is longer than spacer 16 and cover 17 in the length direction. Thus, parts (X portion and Y portion respectively shown in FIG. 2A) of counter electrode 13 and action electrode 14 provided on substrate 12 are exposed.

When biosensor 2 is mounted to a biological sample measurement device, the X portion and the Y portion in FIG. 2A are connected to input terminal 4 disposed in the biological sample measurement device. Due to this connection, biosensor 2 and an electric circuit of the biological sample measurement device may be electrically connected to each other.

Reagent 15 is disposed on substrate 12, and reagent 15 is disposed over counter electrode 13 and action electrode 14. Reagent 15 contains oxidoreductase (for example, glucose oxidase or glucose hydrogenase), electron acceptor (for example, ferricyanide) or the like. The amount of oxidoreductase is 0.01 to 100 U, for example, for each sensor or for one-time measurement, preferably 0.05 to 10 U, and more preferably 0.1 to 5 U. Further, the amount of electron acceptor is 0.1 to 1000 mM for each sensor or for one-time measurement, preferably 1 to 500 mM, and more preferably 10 to 200 mM.

FIG. 2A (top view of biosensor 2) shows action electrode 14 in groove 18, but in many cases, the top surface of action electrode 14 is covered with reagent 15, and thus cannot be visually seen from the top in an actual product.

Groove 18 is formed in spacer 16. Further, a capillary that is a supply path of blood (liquid biological sample) is formed by groove 18, substrate 12 and cover 17. Cover 17 is stacked on spacer 16 so as to cover groove 18 of spacer 16. Air hole 19 is formed in cover 17 so as to communicate with groove 18. Air hole 19 may be disposed at the behind of the mounting position of reagent 15 in biosensor 2. Air hole 19 makes blood (liquid biological sample) or the like provided in a tip end (left side in FIGS. 2A to 2C) of the capillary smoothly penetrate up to reagent 15 by the capillary phenomenon.

The blood (liquid biological sample) provided in biosensor 2 penetrates into groove 18 that forms the capillary by the capillary phenomenon, and reaches reagent 15 to dissolve reagent 15. Then, reaction is produced between a component of reagent 15 and glucose in the blood. In the vital information measurement device of the present embodiment, a blood-sugar level or the like is calculated on the basis of the reaction.

[Measurement Flow]

Biosensor 2 shown in FIGS. 2A to 2C is kept in a drying container before use (not shown). Whenever the blood-sugar level is measured, biosensor 2 is extracted from the drying container one by one. The extracted biosensor 2 is inserted into insert port 3 with making one end side of the biosensor (the side of X portion and Y portion in FIG. 2A) ahead, before being supplied with blood of a user that is a biological sample, and is then mounted to the biological sample measurement device (see FIG. 1). Counter electrode 13 and reaction electrode 14 of the mounted biosensor 2 are electrically connected to input terminals 4 of the biological sample measurement device, respectively (see FIG. 1).

Hereinafter, the measurement flow of the vital information including determination by the mounted biosensor will be described with reference to two embodiments.

Embodiment 1

Figure 3:
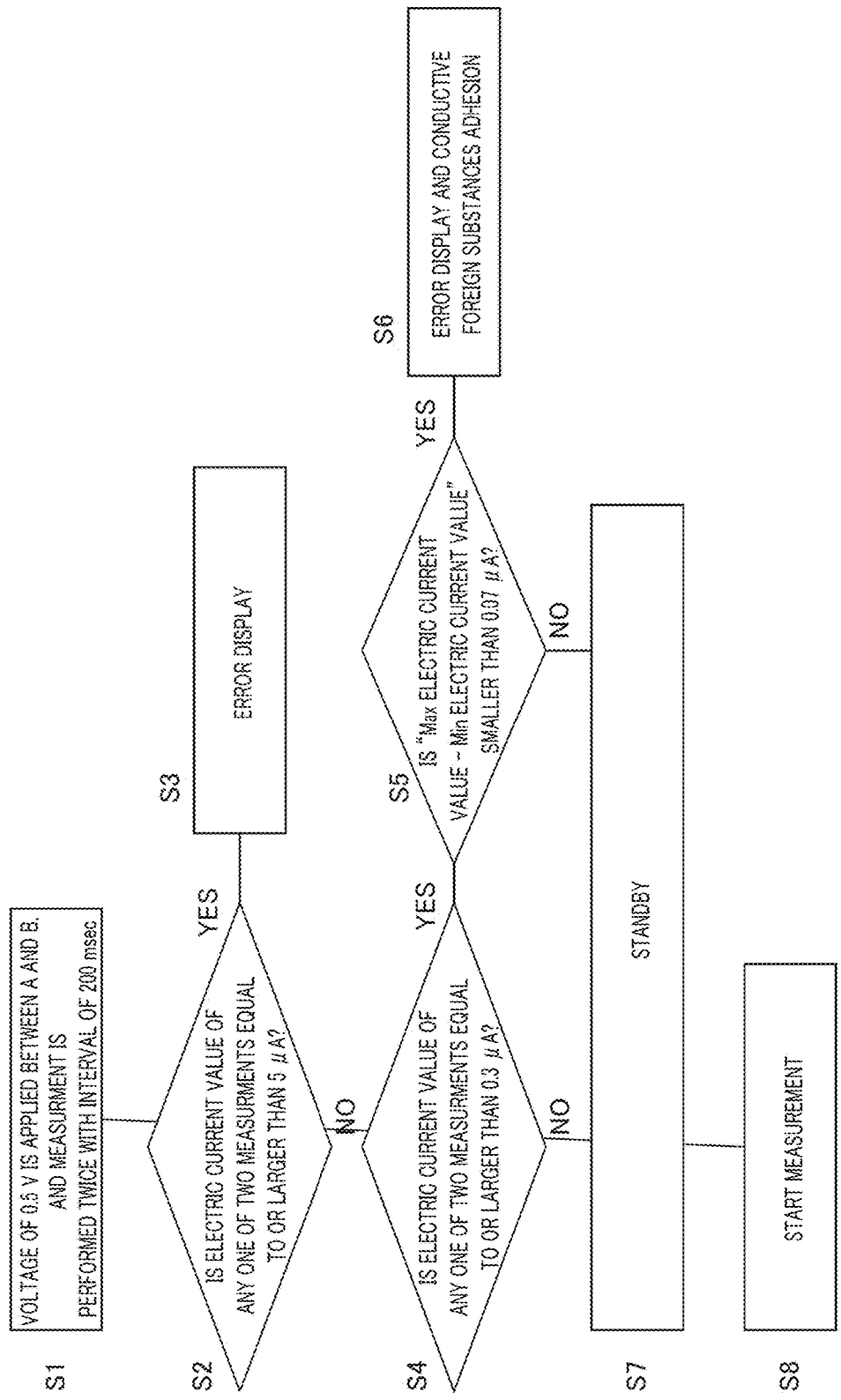
FIG. 3 is a flowchart illustrating a biological sample measurement method according to an embodiment of the invention.

FIG. 3 shows the flow from the time when biosensor 2 is electrically connected to input terminal 4 to the time when the blood-sugar level measurement is started. Control section 7 applies voltage between counter electrode 13 and action electrode 14 of biosensor 2 that is electrically connected to input terminal 4 through voltage application section 5 and input terminal 4 (S1 in FIG. 3). If voltage is applied, electric current flows between counter electrode 13 and reaction electrode 14 of biosensor 2. The electric current is converted into voltage by current-voltage converter section 6, and is then converted into a digital value by A/D converter section 8 (see FIG. 1).

A value of electric current flowing in the biosensor may be set to various measurement values (first measurement value and second measurement value) to be compared with various threshold values to be described later, but it is preferable that values obtained by conversion of the electric current values be set to various measurement values (first measurement value and second measurement value) to be compared with various threshold values to be described later. Normally, after the various measurement values are calculated, the first to third determinations to be described later are performed. In S1 in FIG. 3, the first measurement value and the second measurement value are measured with an interval of 200 msec.

The size of voltage A applied in S1 in FIG. 3 and the application time thereof are shown in FIG. 4. The size of the applied voltage A is in the range of 0.05 to 1 V, for example, preferably in the range of 0.1 to 0.8 V, and more preferably in the range of 0.2 to 0.5 V. When the application time of voltage A is a predetermined time or longer, it is easy to perform the determination. The application time may be 100 msec or longer, for example, and may be about 200 msec. As described above, voltage A applied in S1 in FIG. 3 should not necessarily be formed by one pulse, and may be formed by a plurality of pulses.

Figure 5:
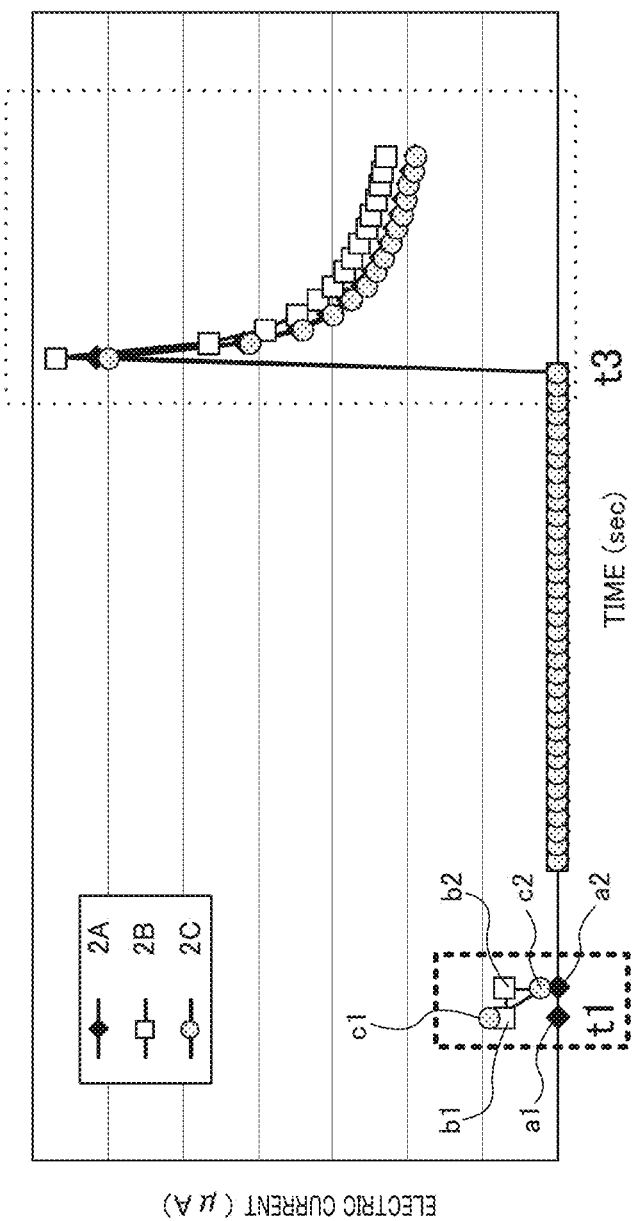
FIG. 5 is a graph illustrating a profile of electric current flowing in a biosensor when the voltage shown in the graph of FIG. 4 is applied to the biosensor (Embodiment 1)
Figure 6:
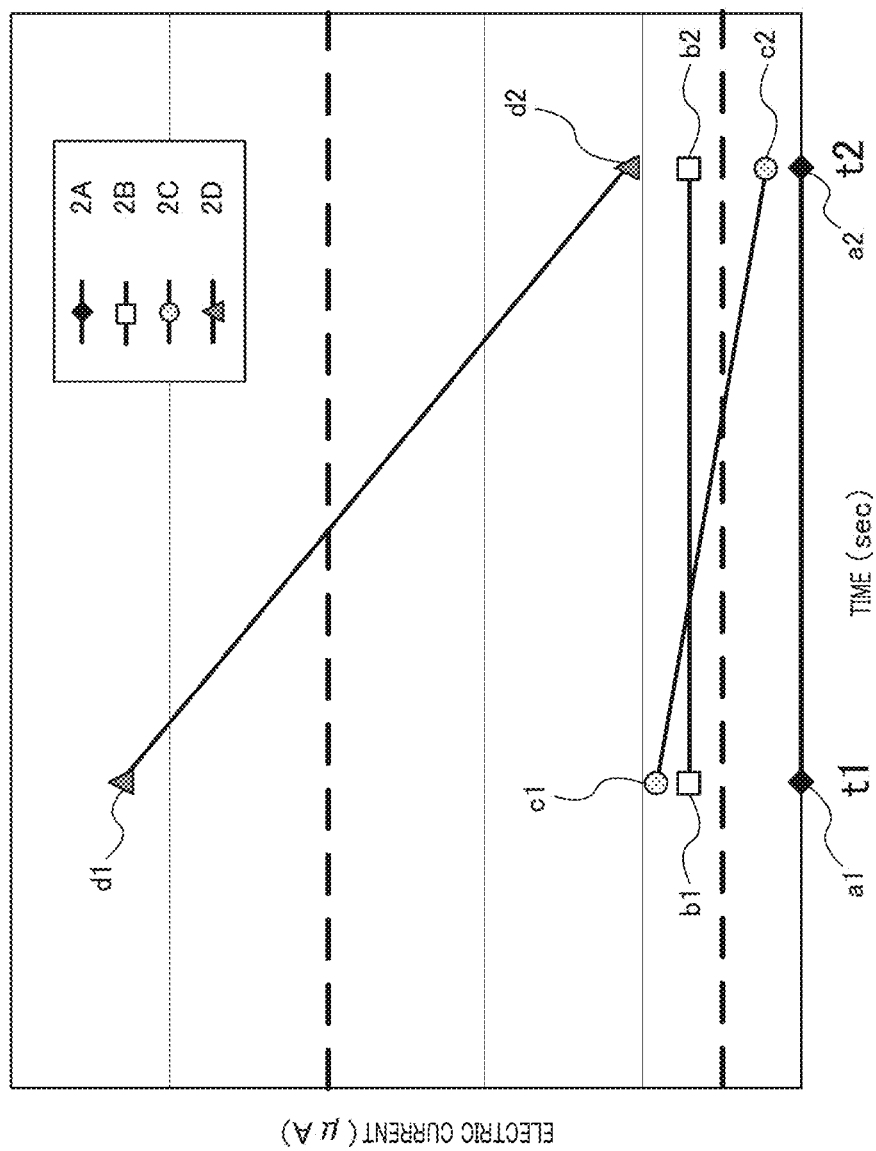
FIG. 6 is an enlarged graph of a region surrounded by a broken line in the graph of FIG. 5.

FIG. 5 shows the relationship between a value of electric current (Y axis) flowing between counter electrode 13 and action electrode 14 of biosensors 2A to 2C and elapsed time (X axis) (the result of biosensor 2D is omitted). FIG. 6 is an enlarged diagram of a broken line region in FIG. 5, and shows the relationship between a value of electric current (Y axis) flowing between counter electrode 13 and action electrode 14 of biosensors 2A to 2D and elapsed time (X axis).

When voltage A (see FIG. 4) is applied, that is, at time t1 (see FIG. 6), electric current flowing between counter electrode 13 and action electrode 14 of biosensors 2A to 2D is shown in a broken line region in FIG. 5 and FIG. 6 (see point a1, point b1, point c1 and point d1). It can be understood that electric current hardly flows between counter electrode 13 and action electrode 14 of biosensor 2A (see point a1). When voltage A is applied, since a biological sample is not supplied to biosensor 2, it is natural that electric current hardly flows between counter electrode 13 and action electrode 14. Accordingly, it can be understood that biosensor 2A is a usable biosensor.

On the other hand, as shown in FIG. 6, it can be understood that when voltage A is applied, electric current flows in biosensors 2B to 2D (see point b1, point c1 and point d1). According to the invention, it is determined whether these biosensors are usable.

Point b1 represents a state where electric current slightly flows since conductive powder is adhered to counter electrode 13 or action electrode 14 of biosensor 2B, for example. The conductive powder may be conductive powder generated when counter electrode 13 and action electrode 14 are in contact with input terminal 4.

Point c1 represents a state where since biosensor 2C is extracted from the drying container and is left as it is for a while, for example, reagent 15 adsorbs moisture to express conductivity.

Point d1 represents a state where since a drop of water is adhered to reagent 15 of biosensor 2D extracted from the drying container, for example, reagent 15 expresses high conductivity.

As described above, electric current (point a1 to ad) flowing in biosensor 2 is converted into voltage by current-voltage converter section 6, and is then converted into a digital value by A/D converter section 8 in order to obtain the first measurement value (see FIG. 1). Determination section 9 compares the obtained first measurement value with the first threshold value to perform the first determination (S2 in FIG. 3). For example, it is determined whether the obtained converted value is equal to or larger than 150 mV that is the first threshold value in comparison. The first threshold value 150 mV corresponds to an electric current value of 5 μA.

In the first determination, it is determined that the converted value (first measurement value) obtained from the electric current of point d1 is larger than the first threshold value. Thus, it is determined that biosensor 2D in which the electric current of point d1 in FIG. 6 flows is unusable, and the information that biosensor 2D is unusable is displayed (error display) on display section 10 through control section 7 (S3 in FIG. 3). In a case where the error display is performed in S3, a user removes biosensor 2D from input terminal 4 and again connects new different biosensor 2 to input terminal 4.

On the other hand, it is determined that the converted value (first measurement value) obtained from the electric current value of point a1 to point c1 is smaller than the first threshold value in comparison. Thus, determination section 9 compares the converted value (first measurement value) obtained from the electric current of point a1 to point c1 with the second threshold value, so as to perform the second determination with respect to biosensors 2A to 2C (S4 in FIG. 3). It is determined whether the obtained converted value (first measurement value) is equal to or larger than 10 mV that is the second threshold value. The second threshold value 10 mV corresponds to an electric current value of 0.3 µA.

In the second determination, it is determined that the converted value (first measurement value) obtained from the electric current of point a1 is smaller than the second threshold value in comparison. In this case, it is determined that a suitable biosensor is mounted in the biological sample measurement device, and the biosensor waits for adhesion of the biological sample (S7 in FIG. 3). In the second determination, it is determined that the converted value (first measurement value) obtained from the electric current of point b1 and point c1 is larger than the second threshold value.

A value of electric current flowing in biosensor 2A to 2C after voltage is further applied for a predetermined time is also measured. Among biosensors 2A to 2C, biosensors 2B and 2C is subjected to the following third determination, biosensors 2B and 2C being determined that the first measurement value is larger than the second measurement value in the second determination.

Electric current of point b2 flows in biosensor 2B at time t2. Electric current of point c2 flows in biosensor 2C at time t2.

Determination section 9 compares difference X (b1–b2) between the converted value (first measurement value) obtained from the electric current of point b1 and the converted value (second measurement value) obtained from the electric current of point b2 with the third threshold value to perform the third determination, with respect to biosensor 2B (S5 in FIG. 3). For example, it is determined whether difference X (b1–b2) is smaller than the third threshold value. The third threshold value is normally set to 10 mV or lower, and may be set to about 2 mV. The third threshold value 2 mV corresponds to an electric current of 0.07 µA. Similarly, determination section 9 compares difference X (c1–c2) between the converted value (first measurement value) obtained from point c1 and the converted value (second measurement value) obtained from point c2 with the third threshold value to perform the third determination, with respect to biosensor 2C (S5 in FIG. 8).

In a case where the plurality of second measurement values is measured for respective different times, in the third determination, the maximum difference among differences X between the first measurement and the plurality of second measurements may be compared with the third threshold value.

In a case where the obtained difference is smaller than the third threshold value in comparison, control section 7 displays the information that biosensor 2 is unusable on display section 10 (S6 in FIG. 3).

In biosensor 2C, the second measurement value (converted value from the electric current of point c2) decreases, compared with the first measurement value (converted value from the electric current of point c1). That is, the difference (c1–c2) is relatively large. In this way, the phenomenon that the second measurement value decreases compared with the first measurement value refers to a phenomenon where a noise component such as a little moisture absorbed in reagent 15 is removed by voltage application. Accordingly, even though vital information (blood-sugar level) is measured by biosensor 2C, a large noise component is not generated, and thus, an accurate measurement value is obtained. It is determined that biosensor 2C is usable.

On the other hand, in biosensor 2B, the second measurement value (point b2) is approximately constant and is not changed, compared with the first measurement value (point b1). In this way, the phenomenon that the first measurement value (point b1) and the second measurement value (point b2) become constant refers to a phenomenon that an electric current slightly flows, the electric current caused by conductive power adhered to counter electrode 13 or action electrode 14 that is connected to input terminal 4 as described above. Differently from the sensor to which moisture is adsorbed, in the sensor to which conductive power is adhered, the electric current value does not decrease by voltage application. Thus, if vital information (blood-sugar level) is measured by biosensor 2B, a noise component is incorporated in the original measurement value, and thus, an accurate measurement value is not obtained. Thus, it is determined that biosensor 2B is unusable.

In this way, in the vital information measurement device according to Embodiment 1, biosensor 2A and biosensor 2C are in a standby state to be provided as suitable biosensor 2 (S7 in FIG. 3).

In the case of the standby state, blood is provided to a flow path of biosensor 2 (see FIGS. 2A to 2C). The provided blood penetrates into the flow path by the capillary phenomenon and dissolves reagent 15. Further, after the blood dissolves reagent 15, blood-sugar level measurement voltage B (see FIG. 4) is applied between counter electrode 13 and action electrode 14 (S8 in FIG. 3). Voltage B in FIG. 4 represents blood-sugar level measurement value voltage applied between counter electrode 13 and action electrode 14. Voltage B is 0.05 to 1 V, preferably 0.1 to 0.8 V, and more preferably 0.2 to 0.5 V.

Electric current according to the blood-sugar level included in blood flows between counter electrode 13 and action electrode 14, the blood-sugar level is measured by control section 7 on the basis of the electric current value, and the measured blood-sugar level is displayed on display section 10.

A dotted line region in FIG. 5 represents a profile of electric current flowing in biosensors 2A to 2C when voltage B in FIG. 4 is applied. As indicated in the dotted line region in FIG. 5, it can be understood that the electric current profiles of biosensor 2A and biosensor 2C approximately match with each other but the electric current profile of biosensor 2B is deviated from the electric current profiles of biosensor 2A and biosensor 2C. That is, the electric current profile of biosensor 2B shows an electric current value higher than the electric current profiles of biosensor 2A and biosensor 2C.

Measurement using biosensor 2B in this way results in measurement with low reliability. On the other hand, it can be understood that biosensor 2C is capable of performing measurement with high reliability although unnecessary electric current is recognized in the initial state (see point c1).

As described above, according to the invention, it is possible to select only suitable biosensors 2 to measure vital information, and thus, a measurement method with high reliability is provided.

Embodiment 2

In Embodiment 1, determination section 9 performs the second determination with respect to biosensors 2A to 2C by comparing the converted value (first measurement value) obtained from the electric current of point a1 to point c1 with the second threshold value (S4 in FIG. 3). In Embodiment 2, the second determination is performed by comparing the converted value (second measurement value) obtained from the electric current value of points a2 to c2 with the second threshold value. Further, in Embodiment 2, the biosensor is subject to the third determination, the biosensor being determined that the second measurement value is equal to or larger than the second threshold value in the second determination. The other configuration is the same as in Embodiment 1.

Embodiment 3

Figure 7:
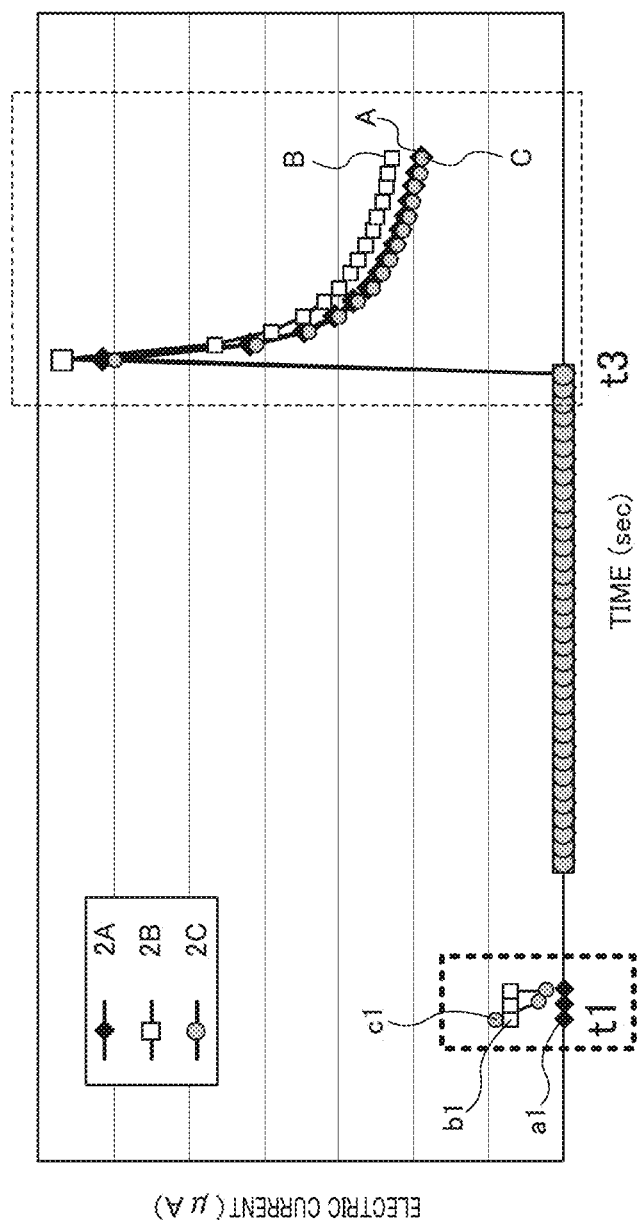
FIG. 7 is a graph illustrating a profile of electric current flowing in a biosensor when the voltage shown in the graph of FIG. 4 is applied to the biosensor (Embodiment 2)
Figure 8:
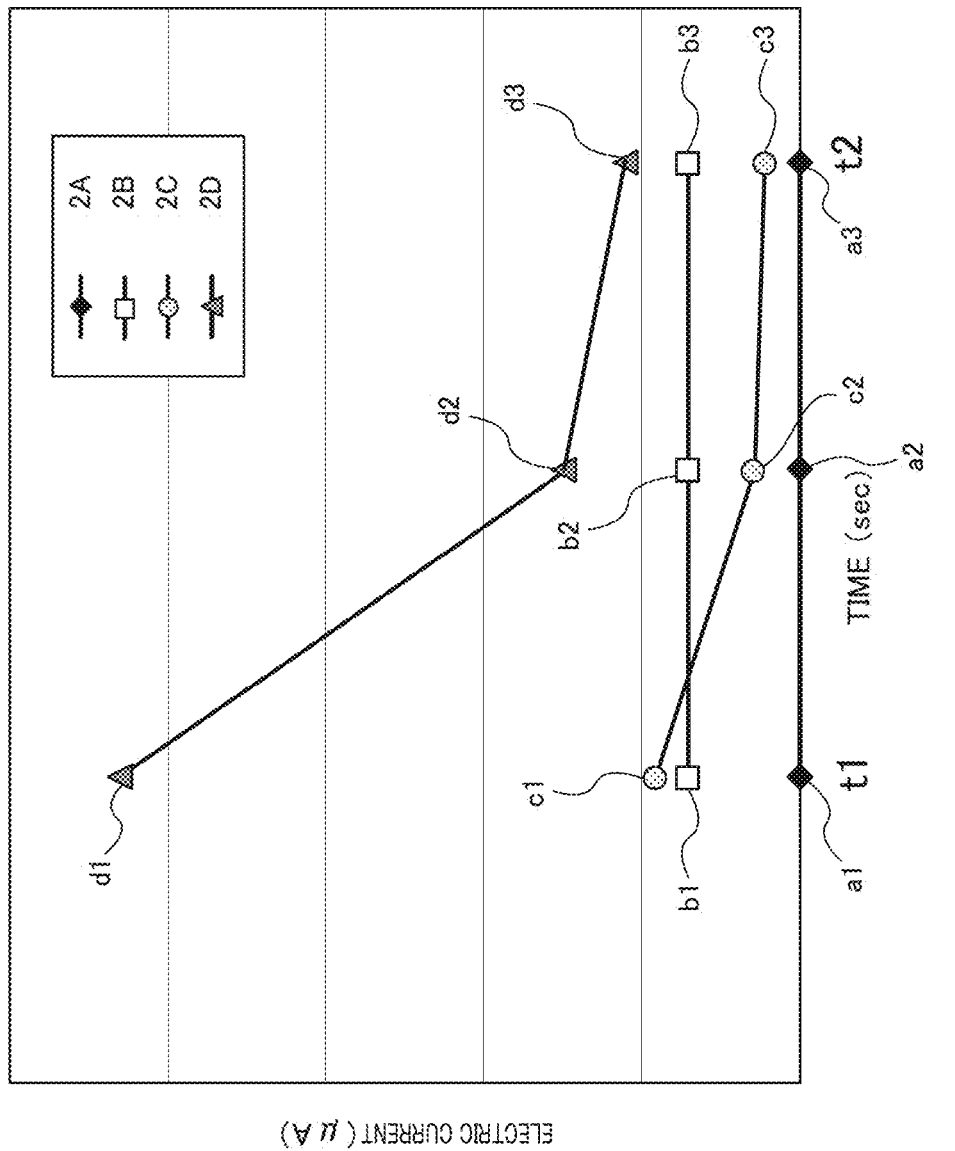
FIG. 8 is an enlarged graph of a region surrounded by a broken line in the graph of FIG. 7.

In Embodiments 1 and 2, the measurement section calculates two measurement values (first measurement value and second measurement value), but in Embodiment 3, the measurement section calculates three measurement values (first measurement value, second measurement value and third measurement value). FIG. 7 shows the relationship between a value of electric current (Y axis) flowing between counter electrode 13 and reaction electrode 14 of biosensors 2A to 2C, and elapsed time (X axis) (the result of biosensor 2D is omitted). FIG. 8 is an enlarged diagram of a broken line region in FIG. 7, and shows the relationship between a value of electric current (Y axis) flowing between counter electrode 13 and reaction electrode 14 of biosensors 2A to 2D and elapsed time (X axis). The same configuration as in Embodiment 1 will be omitted in description of Embodiment 3.

Normally, in a similar way to Embodiment 1, some measurement values (first measurement value, second measurement value and third measurement value) are calculated, and then, the first to third determinations to be described later are performed. Further, in a similar way to Embodiment 1, voltage A (see FIG. 4) may be formed by one pulse or a plurality of pulses. Further, a plurality of the second measurement value or a plurality of the third measurement value may be measured for respective different times.

In a similar way to Embodiment 1, the first measurement value is calculated with respect to biosensors 2A to 2D. Specifically, the converted value of the electric current value of point a1 to d1 is calculated. The calculated converted value (first measurement value) is compared with the first threshold value to perform the first determination (S2 in FIG. 3). As the result of the first determination, it is determined that biosensor 2D in which electric current of point d1 flows is unusable.

Next, the second determination is performed with respect to biosensors 2A to 2C (S4 in FIG. 3). When a predetermined time elapses while continuously applying voltage A in FIG. 4, electric current flowing in biosensors 2A to 2C is measured (see point a2, point b2 and point b3). Voltage A may be formed by one pulse or a plurality of pulses. A converted value of the measured electric current value is calculated and is used as the second measurement value. The second measurement value is compared with the second threshold value to perform the second determination (S4 in FIG. 3). As the result of the second determination, biosensor 2A in which electric current of point a2 flows is usable, and enters the standby state (S7 in FIG. 3).

On the other hand, as the result of the second determination, since the converted value (second measurement value) from the electric current of point b2 and point c2 is equal to or larger than the second threshold value in comparison, biosensor 2B and biosensor 2C is subject to the third determination (S5 in FIG. 3). In the third determination, when a predetermined time elapses while further continuously applying voltage A in FIG. 4, electric current flowing in biosensors 2B and 2C is measured (point b3 and point c3). Voltage A may be formed by one pulse or a plurality of pulses. A converted value of the measured electric current value is calculated and is used as the third measurement value.

Next, "difference Y between the first measurement value and the third measurement value" or "difference Z between the second measurement value and the third measurement value" are calculated. Difference Y of biosensor 2B means "converted value of electric current of point b1—converted value of electric current of point b3". Difference Z of biosensor 2B means "converted value of electric current of point b2—converted value of electric current of point b3."

In a case where the plurality of third measurement values is measured for respective different times, the maximum difference among differences Y between the first measurement value and the plurality of third measurement values is calculated, and the maximum difference among differences Z between the second measurement value and the plurality of third measurement values is calculated.

Further, difference Y or difference Z is compared with the third threshold value to perform the third determination. As the result of the third determination, since difference Y or difference Z of biosensor 2B in which the electric current value is not almost changed is smaller than the third threshold value, control section 7 displays the information that biosensor 2B is unusable on display section 10 (S6 in FIG. 3).

On the other hand, as the result of the third determination, since difference Y or difference Z of biosensor 2C in which the electric current value is reduced with time is larger than the third threshold value, biosensor 2C enters the standby state as a usable biosensor (S7 in FIG. 3).

In this way, blood is provided to biosensors 2A and 2C that are in the standby state and the blood-sugar level measurement is performed, in a similar way to Embodiment 1 (S8 in FIG. 3). Specifically, voltage B in FIG. 4 is applied to the biosensor, electric current flowing between counter electrode 13 and action electrode 14 is measured, the blood-sugar level is measured by control section 7 on the basis of the electric current value, and the measured blood-sugar level is displayed on display section 10.

In a similar way to Embodiment 1, it can be understood that measurement using biosensor 2B results in measurement with low reliability and measurement using biosensors 2A and 2C results in measurement with high reliability (see the dotted line region in FIG. 7). In this way, according to the invention, it is possible to select only suitable biosensor 2 to measure vital information, and thus, to provide a measurement method with high reliability.

INDUSTRIAL APPLICABILITY

According to the invention, it is possible to perform measurement using only a suitable biosensor is performed, and thus, to suppress variation of a measurement value. Accordingly, for example, the technique of the invention is expected to be used as a vital information measurement device that detects vital information such as a blood-sugar level.

REFERENCE SIGNS LIST

1 Main case
2 Biosensor

3 Insert port
4 Input terminal
5 Voltage application section
6 Current-voltage converter section
7 Control section
8 A-D converter section
9 Determination section
10 Display section
11 Power supply
12 Substrate
13 Counter electrode
14 Action electrode
15 Reagent
16 Spacer
17 Cover
18 Groove
19 Air hole
20 Measurement section

The invention claimed is:

1. A vital information measurement device comprising:
an input terminal to which a biosensor is connected;
a display; and
a processor configured to:
apply voltage to the input terminal;
measure a measurement value based on a value of electric current flowing in the biosensor;
measure a first measurement value and a second measurement value based on a value of the electric current flowing in the biosensor when the voltage is applied to the biosensor through the input terminal before a biological sample is supplied to the biosensor, and the second measurement value is a value measured after the first measurement value is measured;
perform a first determination and a second determination to determine whether the biosensor is usable based on results of the first determination and the second determination and the display to display information indicating that the biosensor is usable or unusable for measurement before the biological sample is supplied to the biosensor;
compare the first measurement value with a first threshold value; and
compare the first measurement value or the second measurement value with a second threshold value, wherein the second threshold value is smaller than the first threshold value.

2. The vital information measurement device according to claim 1, wherein the processor is further configured to:
when the first measurement value is smaller than the first threshold value in the first determination, and the second measurement value is smaller than the second threshold value in the second determination,
cause the display to display information indicating that the biosensor is ready for measurement.

3. The vital information measurement device according to claim 1, wherein the processor is further configured to:
when the first measurement value is equal to or larger than the first threshold value in the first determination, cause the display to display information indicating that the biosensor is unusable on the display.

4. The vital information measurement device according to claim 1,
wherein the processor is further configured to:
when the first measurement value is smaller than the first threshold value in the first determination, and the first measurement value or the second measurement value is equal to or larger than the second threshold value in the second determination, perform a third determination.

* * * * *